(12) United States Patent
Tokuhisa et al.

(10) Patent No.: US 7,298,546 B2
(45) Date of Patent: Nov. 20, 2007

(54) ULTRAVIOLET LIGHT SOURCE, LASER TREATMENT APPARATUS COMPRISING ULTRAVIOLET LIGHT SOURCE, AND EXPOSURE APPARATUS COMPRISING ULTRAVIOLET LIGHT SOURCE

(75) Inventors: Akira Tokuhisa, Tokyo (JP); Hiroshi Kitano, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 11/148,428

(22) Filed: Jun. 9, 2005

(65) Prior Publication Data

US 2005/0259314 A1 Nov. 24, 2005

Related U.S. Application Data

(63) Continuation of application No. PCT/JP2003/15772, filed on Dec. 10, 2003.

(30) Foreign Application Priority Data

Dec. 10, 2002 (JP) ............... 2002-357539

(51) Int. Cl.
*H01S 3/00* (2006.01)
*G02F 1/35* (2006.01)
*G03B 27/54* (2006.01)
*G03B 27/72* (2006.01)

(52) U.S. Cl. ............... 359/333; 359/326; 355/67; 355/69

(58) Field of Classification Search ........ 359/326, 359/328, 333, 341.1; 355/67, 69; 372/21, 372/22

See application file for complete search history.

(56) References Cited

U.S. PATENT DOCUMENTS 5,694,408 A 12/1997 Bott et al.
5,790,722 A 8/1998 Minden et al.

(Continued)

FOREIGN PATENT DOCUMENTS

JP 10-41571 2/1998

(Continued)

OTHER PUBLICATIONS

"Efficient 193 nm Generation by Eighth Harmonics of $Er^{<3+>}$-Doped Fiber Amplifier", Kitano, H., et al., Lasers and Electro-optics, 2001 CLEO/PACIFIC RIM 2001. The 4th Pacific RIM Conference, Jul. 15-19, 2001, Piscataway, NJ, USA, IEEE, vol. 2, Jul. 15, 2001, pp. 394-395, paragraph 3; Fig. 1.

(Continued)

*Primary Examiner*—Henry Hung Nguyen
(74) *Attorney, Agent, or Firm*—Morgan, Lewis & Bockius LLP

(57) ABSTRACT

An ultraviolet light source (1) comprises a laser light source (10) for generating a signal light in the infrared region, a optical amplifier (20) which comprises fiber optical amplifiers (21, 22) and amplifies the signal light generated by the laser light source (10), and a wavelength converting optical system (30) which coverts the signal light amplified by the light amplifier (20) into an ultraviolet light and outputs the converted light. The ultraviolet light source (1) uses a single-mode fiber laser (26) as an excitation light source for at least the fiber optical amplifier (22) at one stage of the optical amplifier (20).

12 Claims, 10 Drawing Sheets

U.S. PATENT DOCUMENTS

| | | |
|---|---|---|
| 6,434,172 B1 | 8/2002 | DiGiovanni et al. |
| 6,556,343 B1 * | 4/2003 | Fludger et al. .......... 359/341.3 |
| 6,590,698 B1 | 7/2003 | Ohtsuki et al. |
| 6,894,826 B2 * | 5/2005 | Doi ............................ 359/326 |
| 6,947,123 B1 * | 9/2005 | Ohtsuki ....................... 355/67 |
| 2002/0025097 A1 * | 2/2002 | Cooper et al. ................ 385/12 |
| 2002/0163711 A1 * | 11/2002 | Masum-Thomas ......... 359/334 |
| 2003/0025890 A1 * | 2/2003 | Nishinaga .................... 355/53 |
| 2003/0065312 A1 | 4/2003 | Owa et al. |
| 2003/0072056 A1 * | 4/2003 | Ota ............................ 359/124 |
| 2003/0112835 A1 * | 6/2003 | Williams et al. ............... 372/6 |
| 2004/0086004 A1 * | 5/2004 | Bonaccini et al. ............. 372/6 |
| 2004/0160662 A1 | 8/2004 | Doi |

FOREIGN PATENT DOCUMENTS

| | | |
|---|---|---|
| JP | 11-14551 | 1/1999 |
| JP | 2000-200747 | 7/2000 |
| JP | 2001-66650 | 3/2001 |
| JP | 2001-353176 | 12/2001 |
| WO | WO 02/065597 | 8/2002 |

OTHER PUBLICATIONS

"158-MUJ Pulses From a Single Transverse-Mode, Large-Mode-Area Erbium", Taverner, D. et al., Optics Letters, OSA, Optical Society of America, Washington, D.C., US vol. 22, No. 6, Mar. 15, 1997, pp. 378-380, XP000690331, ISSN: 0146-9592, p. 379, left-hand column, paragraph 1; Fig. 1.

* cited by examiner

ULTRAVIOLET LIGHT SOURCE, LASER TREATMENT APPARATUS COMPRISING ULTRAVIOLET LIGHT SOURCE, AND EXPOSURE APPARATUS COMPRISING ULTRAVIOLET LIGHT SOURCE

This is a continuation of PCT/JP/2003/015772 filed Dec. 10, 2003, which is hereby incorporated by reference.

TECHNICAL FIELD

The present invention relates to an ultraviolet light source that amplifies signal light in an infrared-to-visible range by a fiber optical amplifier and converts the amplified light into ultraviolet light as an output by a wavelength-converting optical system. The present invention relates also to laser treatment apparatus and to exposure apparatus, each apparatus comprising an ultraviolet light source, respectively.

BACKGROUND TECHNOLOGY

Nowadays, ultraviolet laser lights, which have short wavelengths and high temporal coherence, are used in various fields. For example, ultraviolet laser light are used in exposure apparatus in semiconductor-device and in surgical and laser treatment apparatus for such operations as performed in surgery, ophthalmology and dentistry. Ultraviolet laser light are used also in various measuring instruments and analyzers and in processing apparatus. Ultraviolet light sources used in such apparatus include KrF excimer laser, which has an oscillation wavelength at $\lambda=248$ nm, and ArF excimer laser, which has an oscillation wavelength at $\lambda=193$ nm. Although these excimer lasers are already comprised as light sources in various apparatus, they have problems of troublesome maintenance and high running costs because these lasers use fluorine gas as an operational medium besides their being expensive and large in size.

Therefore, a study has been eagerly conducted for an all solid state ultraviolet light source that comprises as a signal light source a solid state laser oscillating in an infrared-to-visible range, that amplifies the light output from the solid state laser by a fiber optical amplifier, and that converts the amplified light into ultraviolet light having a predetermined wavelength as an output by a wavelength-converting optical system. As such an all solid state ultraviolet light source, a proposed ultraviolet light source comprises as a signal light source a DFB semiconductor laser oscillating stably in a band at wavelength $\lambda=1.55$ μm, amplifies the light output from the semiconductor laser to a desired light intensity by an erbium-doped fiber amplifier (hereinafter abbreviated to "EDFA"), and converts the amplified light to ultraviolet light having a wavelength $\lambda=193$ nm, which is the eighth harmonic, as an output by a wavelength-converting optical system, which comprises a crystal for wavelength conversion (refer to, for example, Japanese Laid-Open Patent Publication No. 2000-200747 and No. 2001-353176).

As EDFAs used in such an all solid state ultraviolet light source, known are a single-clad EDFA, which excites an erbium-doped single-clad and single mode fiber (EDF) by a semiconductor laser of single mode oscillation, and a double-clad EDFA, which excites a double-clad EDF by a semiconductor laser of multi-mode oscillation (refer to, for example, Japanese Laid-Open Patent Publication No. 2000-200747 and No. 2001-353176).

Yet, prior-art EDFAs such as those mentioned above have the following problems. First of all, for a single-clad EDFA, the optical power of the single mode oscillation semiconductor laser that excites the EDFA is limited within a range of hundreds of mW, which is comparatively low, so signal light at a low repetition frequency of a few kHz and at a low duty must be used to generate a peak power higher than 10 kW (with a pulse width of up to 1 ns). The light output from the EDFA in this case, even if a high peak power is gained, achieves only a relatively low power of about 100 mW at the most as an average power. This is a problem indicating that the original amplifying ability of the fiber optical amplifier is not utilized fully.

Also, in a fiber-optical amplifier like that described above, it is a common practice to arrange a plurality of EDFAs in series connection in a multiple stage construction to achieve a predetermined peak power. However the ASE lights generated in the EDFA are added as DC noises to the signal-less parts between adjacent signal pulses, which leads to a significant reduction in the signal-to-noise ratio of the output signal. Therefore, as an arrangement for removing DC noise components in a multi-staged EDFA, an electro-optic modulating element or an acousto-optic modulating element is provided between adjacent stages, and each modulating element is controlled to synchronize with a signal light source to supply signal light at a high signal-to-noise ratio to a rear stage EDFA. However, the construction of the EDFA becomes complicated, and the manufacturing cost of the EDFA also grows expensive. In addition, there is a problem of loss in the signal light caused by inserting the modulation elements.

On the other hand, a double-clad EDFA comprises a first clad and a second clad. The first clad surrounds a core doped with a laser medium and functions as a coupler for excitation light, and the second clad is formed around the first clad to provide a waveguide to the first clad. As the first clad has a multi-mode and a relatively large cross-sectional area, it can efficiently couple high-power semiconductor lasers that have multi-mode oscillations, improving the power transmission of the excitation light, and thereby increases the pulse repetition frequency and the average output power. However, in a double-clad EDFA, the excitation efficiency per unit length is lower than a single-clad EDFA, which feeds excitation light directly into the core. Because of this, it is difficult to reduce the length of the fiber in a double-clad EDFA, so there is a problem of an increased loss in the signal light, which is caused by nonlinear effects such as a parametric process or a simulated Raman scattering, occurring in the fiber. As a result, a double-clad EDFA cannot achieve as high a peak power as a single-clad EDFA.

DISCLOSURE OF THE INVENTION

The present invention has been conceived in view of the above mentioned problems and has an objective to provide an ultraviolet light source that has a simple construction and generates both a high peak power and a high average power. It is also an object of the present invention to provide exposure apparatus and laser treatment apparatus, each system comprising such an ultraviolet light source.

To solve the above problems and to achieve the objectives, the present invention provides an ultraviolet light source that comprises a laser light source, which generates signal light in an infrared-to-visible range, a optical amplifier, which includes at least one stage of fiber optical amplifier and amplifies the signal light generated by the laser light source, and a wavelength-converting optical system, which converts the signal light amplified by the optical amplifier into ultraviolet light as an output. In the ultraviolet light source, a single mode fiber laser is used as an excitation light source for at least one stage of fiber optical amplifier in the optical amplifier.

In this ultraviolet light source according to the present invention, it is preferable that the fiber optical amplifier that uses a single mode fiber laser as an excitation light source be a final stage fiber optical amplifier in the optical amplifier.

In the ultraviolet light source, it is also preferable that the single mode fiber laser be a Raman fiber laser.

In this ultraviolet light source, the single mode fiber laser can be a ytterbium-doped (Yb) fiber laser.

Furthermore, the ultraviolet light source may comprise a wavelength division multiplexer, which is provided on the input side of the optical amplifier. In this case, the wavelength division multiplexer is a fiber-fused type and mixes the signal light coaxially with the excitation light output from the excitation light source.

Laser treatment apparatus according to the present invention comprises an ultraviolet light source described above and an irradiation optical system, which leads ultraviolet light emitted from the ultraviolet light source to a treatment site for irradiation.

Exposure apparatus according to the present invention comprises an ultraviolet light source described above, a mask-supporting part, which supports a photomask provided with a predetermined exposure pattern, an object-supporting part, which supports an object to be exposed, an illumination optical system, which leads ultraviolet light emitted from the ultraviolet light source to illuminate the photomask supported by the mask-supporting part, and a projection optical system, which leads the light that has passed through the photomask in the illumination through the illumination optical system, to project the object to be exposed, which is supported by the object-supporting part.

PREFERRED EMBODIMENTS OF THE PRESENT INVENTION

Figure 1:
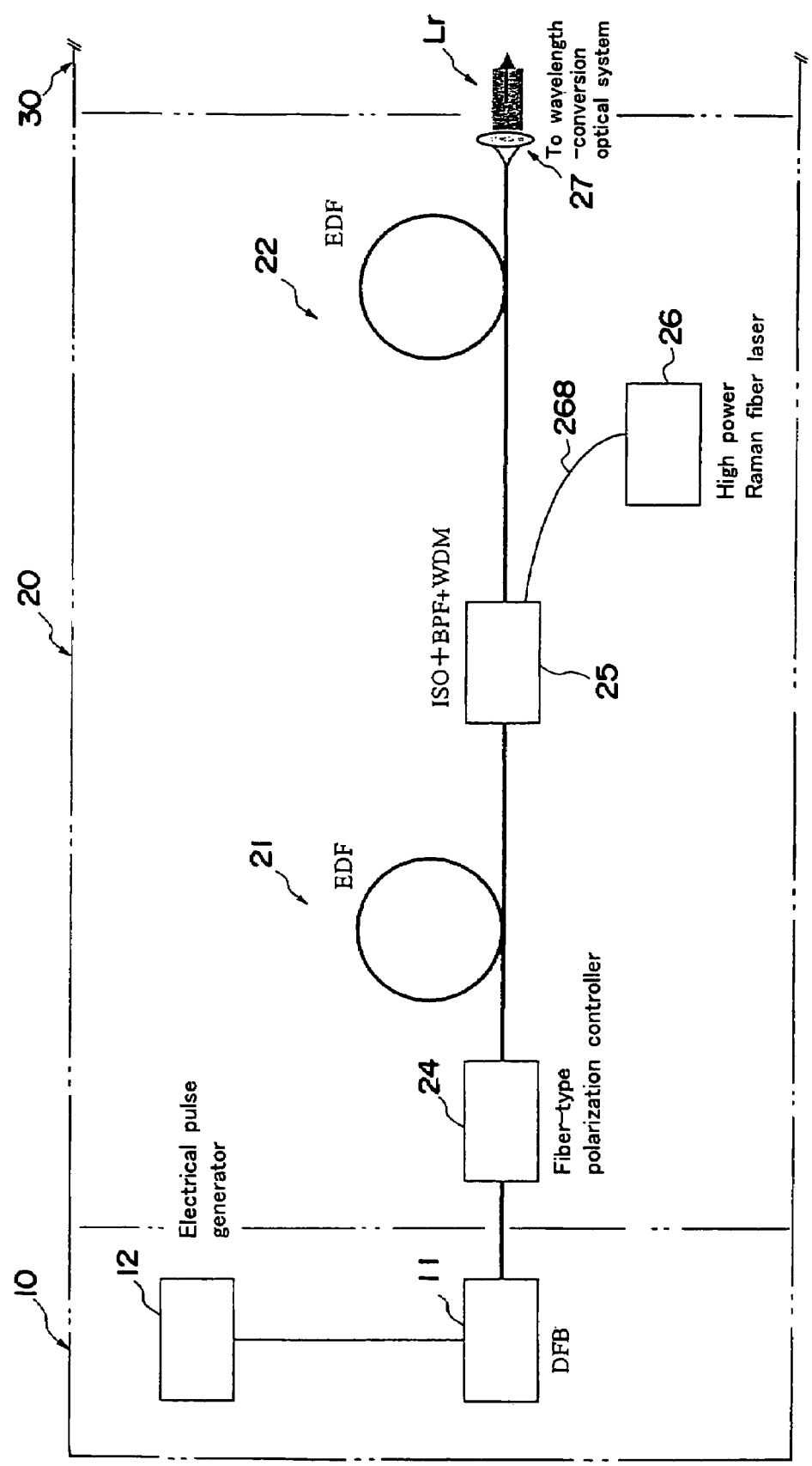
FIG. 1 is a schematic diagram showing a laser light source and a light amplifier of an ultraviolet light source according to the present invention.

Now, preferred embodiments of the present invention are described in reference to the drawings.

Ultraviolet Light Source

At first, an embodiment of an ultraviolet light source according to the present invention is described in reference to FIG. 1~FIG. 4, each of which shows a section of the ultraviolet light source. The ultraviolet light source 1 comprises a laser light source 10, which generates signal light in an infrared-to-visible range, an optical amplifier 20, which includes a front stage fiber optical amplifier 21 and a rear stage fiber optical amplifier 22 and amplifies the signal light generated by the laser light source 10, and a wavelength-converting optical system 30, which converts the signal light amplified by the optical amplifier into ultraviolet light as an output in wavelength conversion. The ultraviolet light source 1 further comprises a single mode fiber laser as an excitation light source 26 for the rear stage fiber optical amplifier 22 of the optical amplifier 20.

The laser light source 10 comprises a solid state laser 11 and a controller 12, which controls the operation of the solid state laser, and the laser light source 10 is a signal light source that outputs signal light in pulses to the light amplifier 20. The solid state laser 11 can be, for example, an InGaAsP, Distributed Feedback (DFB) semiconductor laser, which oscillates at wavelength $\lambda=1.55$ μm in an infrared band. The oscillating wavelength of the above mentioned DFB semiconductor laser has temperature dependency of about 0.1 nm/degree C., so while the semiconductor laser is controlled at constant temperature, it outputs narrow-band infrared light at a single wavelength, for example, $\lambda=1547$ nm. The controller 12, which is a driver that controls the DFB semiconductor laser 11, supplies a driving signal with a pulse width of about 1 ns at repetition-frequency $f=$tens or hundreds kHz to the DFB semiconductor laser 11, so that the DFB semiconductor laser 11 operates in pulse oscillation and outputs a pulse-like signal light at a peak power of about 10 mW to the optical amplifier 20.

An external modulator, for example, an electro-optic modulating element or an acousto-optic modulating element may be used to form optical pulses from an output of the DFB semiconductor laser 11 stably oscillating in CW mode. By such an arrangement, narrow-band signal light with little frequency chirp can be output to the optical amplifier 20.

The optical amplifier 20, which is an amplifier that amplifies the signal light having a wavelength $\lambda=1547$ nm output from the laser light source 10, comprises the above mentioned front stage and rear stage fiber optical amplifiers 21 and 22, a polarization controller 24, a compound module 25, and the above mentioned excitation light source 26, which excites the rear stage fiber optical amplifier 22. In the optical amplifier 20, the front stage and rear stage fiber optical amplifiers 21 and 22 are connected with each other in series.

The polarization controller 24, which is provided at the input part of the optical amplifier 20, is a fiber type polarization controller, and controls the polarization of the signal light to suppress nonlinear processes like four-wave mixing or stimulated Raman scattering, which can occur at the rear stage fiber optical amplifier 22.

The front stage fiber optical amplifier 21 is a preamplifier that amplifies the signal light of a peak power of about 10 mW output from the laser light source 10 up to about 1 kW. As the peak power of the light output is about 1 kW at this preamplifier part, a single clad erbium-doped fiber (EDF) is used as the fiber optical amplifier 21, and the output of a single mode semiconductor laser as excitation light is coupled to the EDF. This excitation light source for the EDF, which constitutes the front stage fiber optical amplifier 21, and a Wavelength Division Multiplexer (WDM), which leads the excitation light to the fiber core are not shown in FIG. 1.

For a stable optical amplification of the peak power from 10 mW to 1 kW (gain 50 dB), it is preferable that the front stage fiber optical amplifier 21 comprise two stages of EDFAs. In this case, between the first stage EDFA and the second stage EDFA, a narrow-band filter is provided to remove ASE, which is generated at the first stage, and an isolator is inserted to suppress the oscillations at the first stage and at the second stage.

On the other hand, it cannot be ignored that the signal gain decreases in the range where the peak power exceeds 1 kW because of nonlinear effects such as four-wave mixing or stimulated Raman scattering. Therefore, it is desirable that the fiber of the fiber optical amplifier 21, if the fiber optical amplifier 21 comprises a single stage, or the fiber of the second stage, if the fiber optical amplifier 21 comprises two stages, be a single clad EDF with high erbium concentration (Er concentration>1000 ppm) and a large mode radius of about 10 μm.

Figure 3:
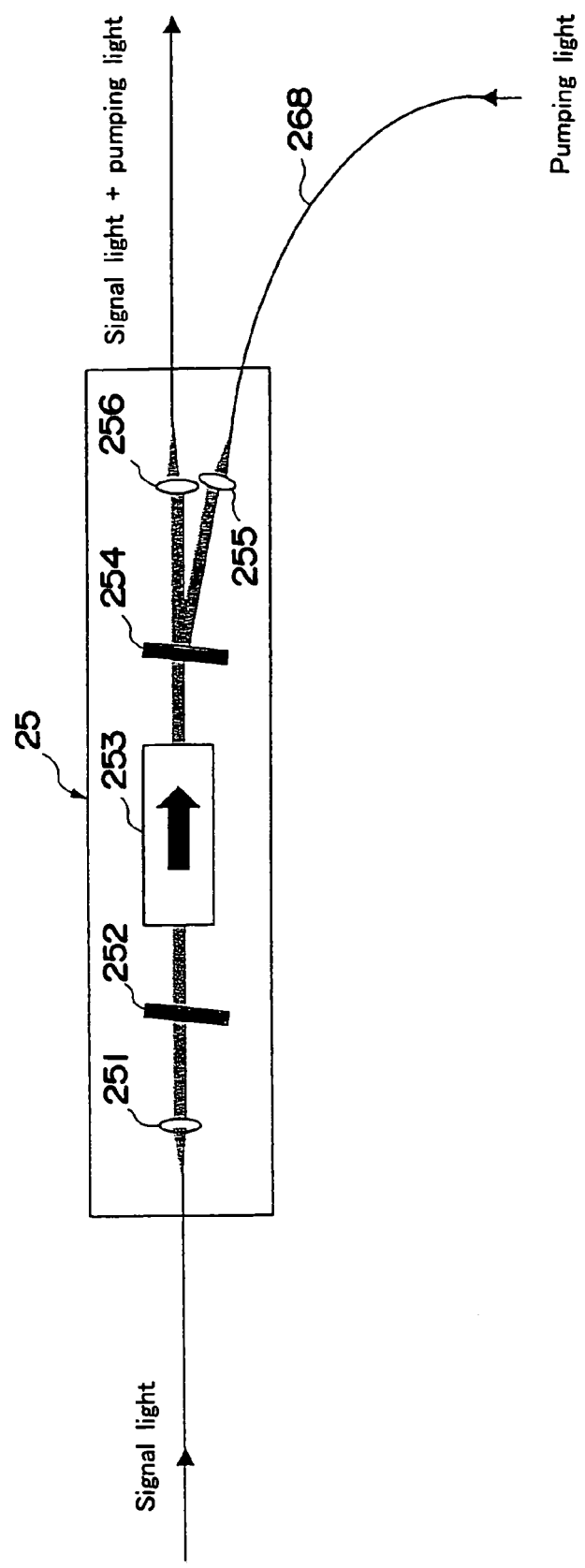
FIG. 3 is a schematic diagram showing a compound module of the light amplifier.

The signal light emitted from the front stage fiber optical amplifier 21 enters the compound module 25, in which a collimator lens 251, a narrow-band filter 252, an isolator 253, a Wavelength Division Multiplexer (WDM) 254, a collimator lens 255, and a condenser lens 256 are assembled together into one unit as shown in FIG. 3.

Here, the narrow-band filter 252 is a filter that passes signal light only within a predetermined transmission bandwidth whose center is at the output wavelength of the DFB semiconductor laser 11. As the narrow-band filter 252, a narrow-band filter with a transmission bandwidth of, for example, about 1 nm is used to remove noise components like ASE that is generated at the front stage fiber optical amplifier 21 and to improve the signal-to-noise ratio of the signal light fed into the rear stage fiber optical amplifier 22. In addition, an isolator 253 is provided to isolate the front stage fiber optical amplifier 21 from the rear stage fiber optical amplifier 22 for preventing oscillation caused by the backward propagation of the light coming from the rear stage fiber optical amplifier 22 and gain reduction caused by multiple reflections of the ASE.

The Wavelength Division Multiplexer (hereinafter referred to as "WDM") 254 is a device that mixes the signal light, which is emitted from the front stage fiber optical amplifier 21 and is collimated by the collimator lens 251, with the excitation light (pumping light), which is led from the excitation light source 26 through a fiber 268 and is collimated by the collimator lens 255. FIG. 3 shows a reflective type WDM, which superposes coaxially the signal light and the excitation light by transmitting the signal light having a wavelength λ=1547 nm, which is emitted from the fiber optical amplifier 21, and by reflecting the excitation light having a wavelength λ=1480 nm, which is led from the excitation light source (Raman fiber laser) 26.

The fiber-type compound module 25, which comprises the above described optical elements as a unit, has a high efficiency because of its design minimizing coupling loss and fusion splice loss. It also avoids nonlinear effect as fibers involved can be shortened.

The excitation light source 26 is a single mode fiber laser, and FIG. 1 shows a Raman fiber laser as an example. The Raman fiber laser 26 is an excitation light source for the rear stage fiber optical amplifier 22 and supplies excitation light having a wavelength λ=1480 nm at a single mode CW power of 10 W through a fiber 268 to the WDM 254. Here, the Raman fiber laser is explained briefly. It is a laser that comprises a ytterbium-doped fiber laser and a cascade Raman resonator including FBGs. The output terminal of the ytterbium-doped fiber laser is connected to the cascade Raman resonator. It can output a laser light at a CW power of up to about 20 W and at wavelength λ=1480 nm in single mode.

Figure 4:
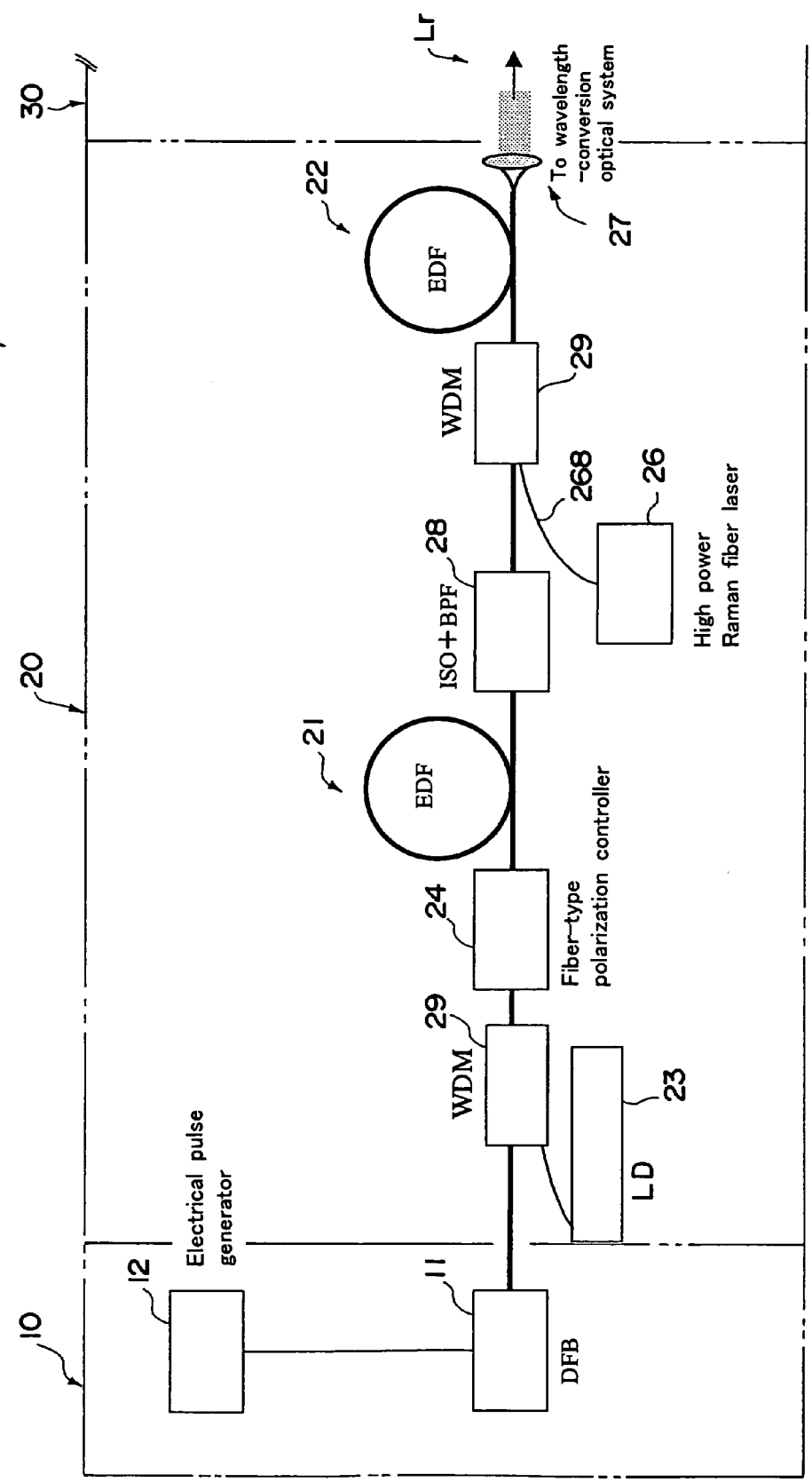
FIG. 4 is a schematic diagram showing a laser light source and a light amplifier of another ultraviolet light source according to the present invention.

If the excitation light source 26 is operated in a range where the excitation light output therefrom exceeds 5 W in CW power, then instead of the reflective type WDM used in the compound module 25 described above, preferably, a fiber-fused type WDM 29 be provided separately in addition to a compound module 28, which comprises an isolator and a band-pass filter as shown in FIG. 4. By this arrangement, the optical amplifier can be durable even in a case where a high power excitation light source is used to generate an average power above 5 W.

In the case where the reflective type WDM 254 is used, the coupling can be done not only by a forward excitation (in which the direction of the excitation light is the same as that of the signal light) but also by a backward excitation (in which the direction of the excitation light is opposite to that of the signal light) as shown in FIG. 1. However, in the case where the fiber-fused type WDM 29 is used as shown in FIG. 4, it is preferable that a forward excitation (in which the direction of the excitation light is the same as that of the signal light) be executed.

If the fiber-fused type WDM 29 is used in a backward excitation, then signal light at a high peak power, which has been amplified, passes through the WDM 29, inducing a nonlinear process. Therefore, it is not possible to achieve a high peak power.

On the other hand, if a forward excitation is executed, then no nonlinear process is induced because signal light at a low peak power before its amplification passes through the WDM. In this case, it is possible to achieve a high peak power.

At the outlet of the EDF, where signal light at a high power passes, even though the power of the excitation light decreases while it passes through the EDF, the Raman fiber laser maintains a sufficiently high power for the signal light relatively and does not interfere with the amplification of the signal light occurring near the outlet.

The signal light emitted from the front stage fiber optical amplifier 21 and the excitation light emitted from the Raman fiber laser 26, which are combined coaxially at the WDM 254 in the above described way, are collected by the condenser lens 256 and then fed into the rear stage fiber optical amplifier 22.

The rear stage fiber optical amplifier 22 is the last stage amplifier, which amplifies the signal light at a peak power of 1 kW after the amplification by the front stage fiber optical amplifier 21 up to a peak power of about 20 kW. This fiber optical amplifier 22 comprises a single clad EDF and operates with single mode high power excitation light, which is fed from the Raman fiber laser 26.

At the rear stage fiber optical amplifier 22, the peak power of the input signal light is a already about 1 KW, which is amplified to become extremely high about 20 KW at the output of the amplifier. Therefore, the EDF comprises a single clad EDF doped with erbium at a high concentration (Er>1000 ppm) and has a large mode diameter greater than about 10 μm to avoid nonlinear process in the fiber.

Figure 5:
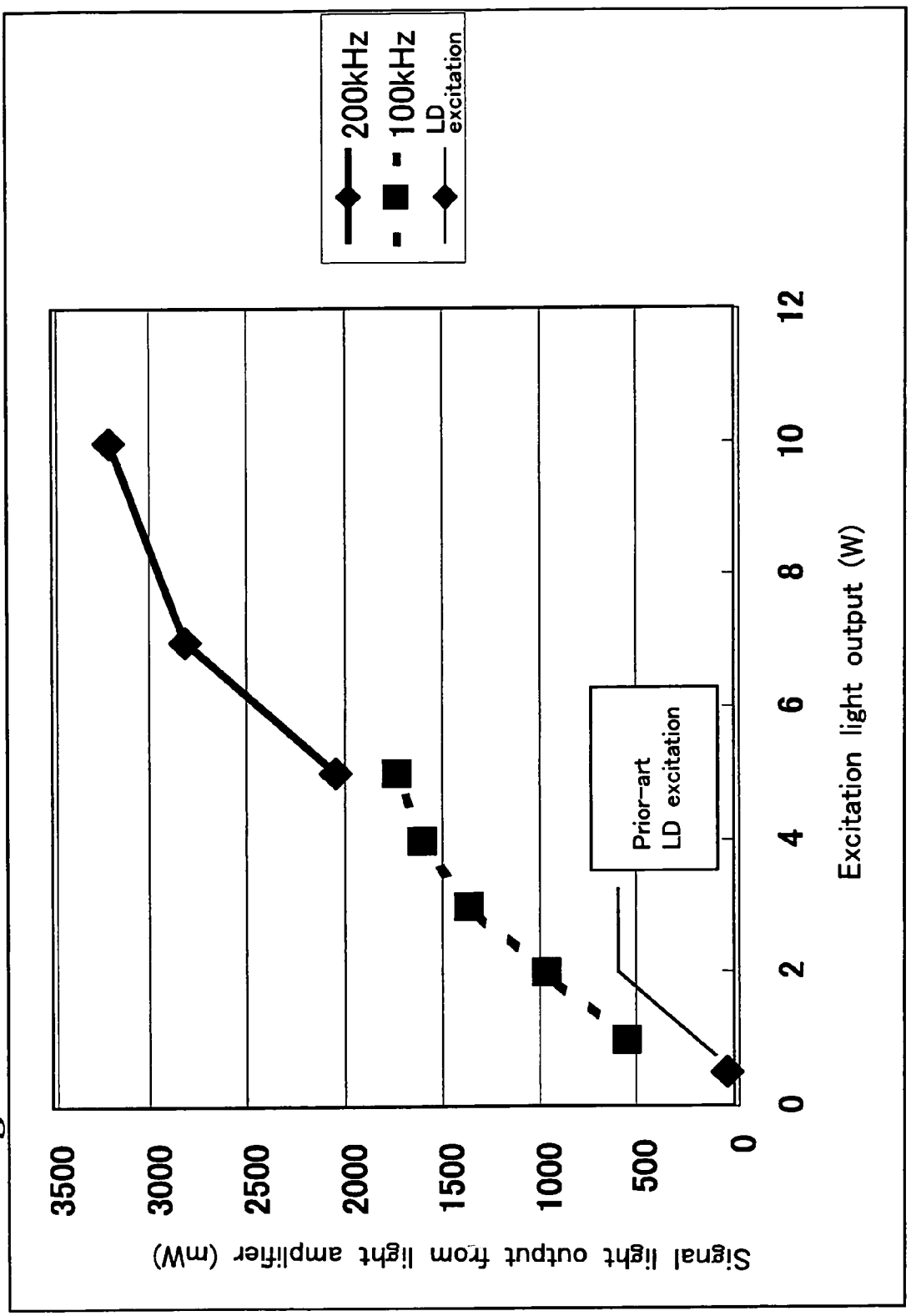
FIG. 5 is a graph describing a relation between the power of the excitation light output from a Raman fiber laser and the power of the signal light output from the light amplifier.

FIG. 5 is a graph describing a relation between the power of the excitation light output from the Raman fiber laser and the power of the signal light (fundamental wave output at 1547 nm) output from the light amplifier. The signal light output from the optical amplifier is controlled by changing the power of the excitation light output from the Raman fiber laser. The repetition-frequencies of the signal light at 100 kHz and at 200 kHz are indicated by (---■---) and by (—◆—), respectively, and an LD excitation is indicated by (--◆--).

In this arrangement, for example, when the power of the excitation light output from the Raman fiber laser 26 is at 10 W, the signal light having a repetition-frequency f=200 kHz with a pulse width of 1 ns and a peak power of 10 mW, which is input from the front stage fiber optical amplifier 21, is amplified to infrared light at a high power with a peak power of 15 kW and an average power of more than 3 W as an output.

By using a high power single mode fiber laser as an excitation light source for the last stage fiber optical amplifier in this way, the optical amplifier can achieve both a high peak power of more than 20 kW and a high average power of more than 2 W. In addition, a single clad and single mode EDF, which has a high excitation efficiency per unit length as EDF, can be used. Therefore, by shortening the fiber length of the EDFA, the device can be made smaller and lighter and the optical amplifier is realized with both a high peak power and a high average power.

Moreover, the pulse-repetition frequency of the signal light can be increased up to hundreds kHz, increasing the pulse signal ON time per unit time and decreasing the pulse signal OFF time per unit time. As a result, the DC noise component in the signal light decreases correspondingly, and the signal-to-noise ratio improves remarkably. Therefore, this system does not need active modulating elements like electro-optic modulating elements or acousto-optic modulating elements, which are provided in a prior-art multi-staged EDFA between adjacent stages to cut the DC noise component, and therefore it does not need a controller that synchronizes the operation of these modulating elements to pulses of the signal light. As a result, the optical amplifier can be simplified substantially, reducing manufacturing cost and realizing a high stabilization.

The above described embodiment discloses an example that uses an EDF whose core is doped only with erbium. However, a Yb-codoped EDF, which is an EDF added with ytterbium (Yb) in addition to erbium, can be also used. In this case, the fiber optical amplifier 22 comprises a ytterbium-doped fiber laser as a single mode fiber laser for the excitation light source 26. The ytterbium-doped fiber laser achieves a CW power of more than 10 W in single mode, so it can constitute a fiber optical amplifier that can output an average power of more than 2 W like the EDFA which comprises a Raman fiber laser as an excitation light source in the above described case.

FIG. 1 and FIG. 4 disclose examples that comprise an LD 23 as an excitation light source for the EDF that constitutes the front stage fiber optical amplifier 21. However, a Raman fiber laser can be used also as an excitation light source for the EDF that constitutes the front stage fiber optical amplifier 21. In this case, a Raman fiber laser, which is different from the Raman fiber laser 26, is provided additionally, or the fiber 268 provided to the Raman fiber laser 26 is branched, and this branch fiber is provided to a compound module (not shown).

Figure 2:
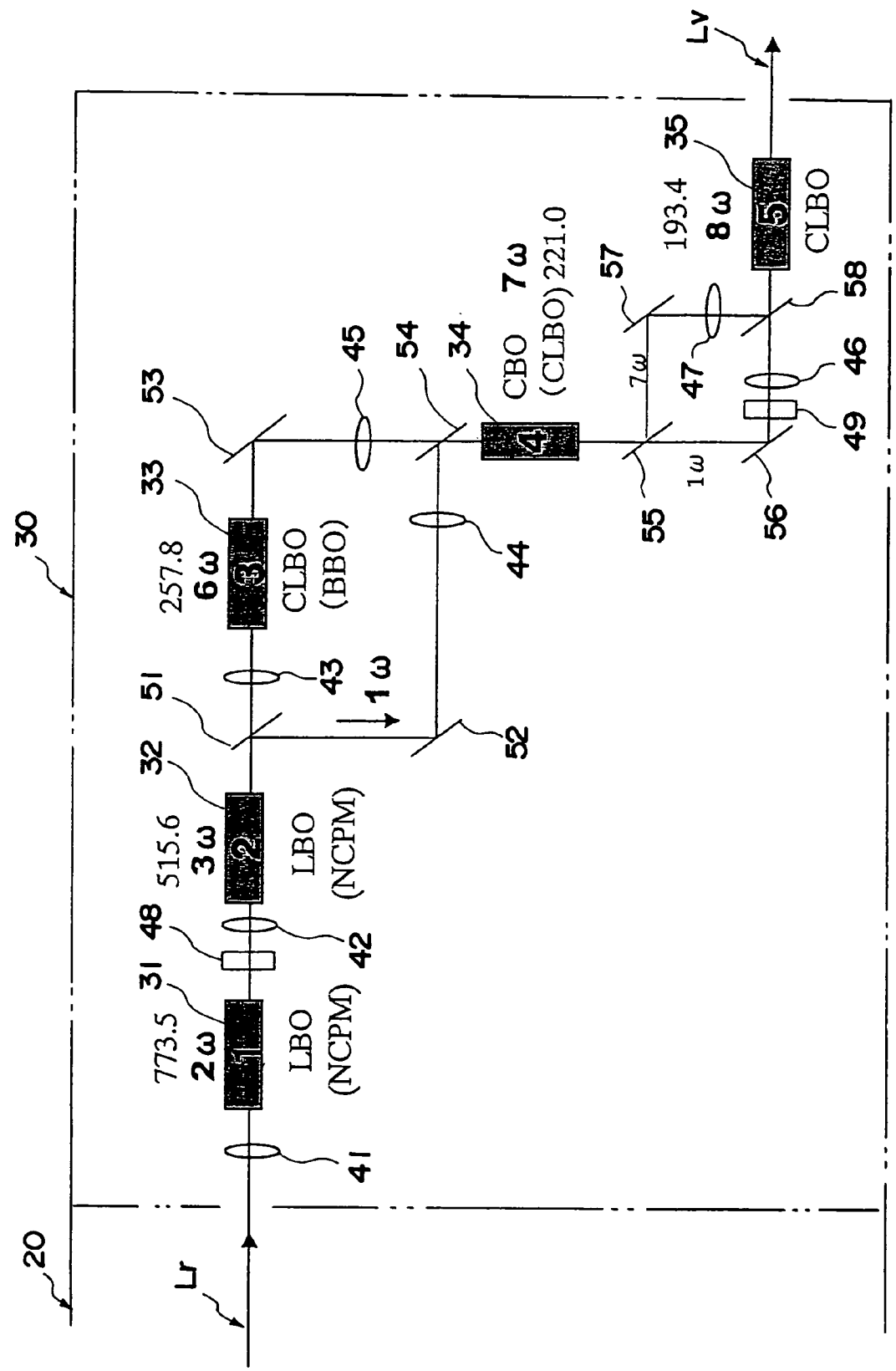
FIG. 2 is a schematic diagram showing a wavelength-converting optical system of the ultraviolet light source.

The signal light having a wavelength $\lambda=1547$ nm amplified by the optical amplifier 20 is collimated once by a collimator lens 27 and then output to the wavelength-converting optical system 30, which is an optical system that converts the signal light in an infrared range coming from the optical amplifier 20 into ultraviolet light. As an example of wavelength-converting optical system that functions in this way, FIG. 2 illustrates an arrangement that converts the signal light (fundamental wave laser light Lr) having a wavelength $\lambda=1547$ nm input from the optical amplifier 20 into an ultraviolet laser light Lv having a wavelength $\lambda=193.4$ nm, which is the eighth harmonic of the fundamental wave, as an output. This diagram is referred to in the following description.

The wavelength-converting optical system 30 comprises wavelength conversion crystals 31~35, lenses 41~47, each of which is provided between adjacent wavelength conversion crystals, respectively, to collect a laser light emitted from a wavelength conversion crystal and to feed it to a next wavelength conversion crystal in line, mirrors 51~58 for separating or combining higher degree harmonics, and wave plates 48 and 49, which adjust polarization.

The fundamental wave laser light Lr having a wavelength $\lambda=1547$ nm input from the optical amplifier 20, which is shown on the left side of the schematic diagram, passes through the wavelength conversion crystals 31, 32, 33, 34 and 35 in the left-to-right direction in the diagram while it is being separated or combined by dichroic mirrors, which have a characteristic of wavelength selectivity. In this process, the fundamental wave ($\lambda=1547$ nm) undergoes wavelength conversion and is converted into the second harmonic ($\lambda=773.5$ nm), into the third harmonic ($\lambda=515.6$ nm), into the sixth harmonic ($\lambda=257.8$ nm), into the seventh harmonic ($\lambda=221$ nm), and into the eighth harmonic ($\lambda=193.4$ nm) in this listed order. Finally, the converted wave is output to the right side of the schematic diagram as ultraviolet laser light Lv having a wavelength $\lambda=194.3$ nm, which corresponds to the eighth harmonic (eighth higher harmonic) of the fundamental wave.

The first wavelength-converting section, which converts the fundamental wave into the second harmonic, comprises an $LiB_3O_5$ crystal (LBO crystal) as the wavelength conversion crystal 31. The phase matching is achieved by tuning the temperature of the LBO crystal (Non-Critical Phase Matching (NCPM)). At the LBO crystal 31, a Second Harmonic Generation (SHG) is performed to generate the second harmonic (frequency $2\omega$, wavelength $\lambda=773.5$ nm), having frequency which is twice of the fundamental wave of the light.

The second harmonic, which has been generated in wavelength conversion at the LBO crystal 31, and the fundamental wave ($\omega$), which has passed through the crystal 31 without wavelength conversion, are led into a wave plate 48, where they are given delays of one wavelength and half a wavelength, respectively, and where only the polarization of the fundamental wave is rotated by 90 degrees. Then, they are passed through a condenser lens (achromat) 42, which makes the light having these two wavelengths incident at the same point of a second wavelength conversion crystal 32.

The second wavelength-converting section comprises an LBO crystal as the wavelength conversion crystal 32, which is used by an NCPM at a temperature different from that for the LBO crystal 31 of the first wavelength-converting section. At the LBO crystal 32, a Sum Frequency Generation (SFG) is performed to generate the third harmonic ($3\omega$, $\lambda=515.6$ nm) from the second harmonic ($2\omega$), which has been generated by the first wavelength-converting section, and the fundamental wave ($\omega$), which has been transmitted without wavelength conversion ($3\omega=2\omega+\omega$).

The third harmonic, which has been generated in wavelength conversion at the LBO crystal 32, and the fundamental wave ($\omega$), which has passed through the crystal 32 without wavelength conversion, are separated by a dichroic mirror 51. The third harmonic ($3\omega$) passes through the dichroic mirror 51 to a condenser lens 43, which collects the light and feeds it to a third wavelength conversion crystal 33. On the other hand, the fundamental wave (ω) is reflected by the dichroic mirror 51 and led through another mirror 52, a condenser lens 44 and another dichroic mirror 54 to a fourth wavelength conversion crystal 34.

The third wavelength-converting section comprises a $CsLiB_6O_{10}$ crystal (CLBO crystal) as the wavelength conversion crystal 33, which is used under angular phase matching condition. At the CLBO crystal 33, a second harmonic generation is performed to generate the sixth harmonic (6ω, λ=257.8 nm), whose frequency is twice of the third harmonic (3ω). The sixth harmonic, which has been generated by the CLBO crystal 33, is led through a mirror 53 and a condenser lens 45 to a dichroic mirror 54, where it is coaxially combined with the fundamental wave (ω), and combined waves are fed into a fourth wavelength conversion crystal 34. Incidentally, a β-$BaB_2O_4$ crystal (BBO crystal) may be used instead of the CLBO crystal.

The fourth wavelength-converting section comprises a $CsB_3O_5$ crystal (CBO crystal) as the wavelength conversion crystal 34, which is used under angular phase matching condition to generate the seventh harmonic (7ω, λ=221 nm) from the fundamental wave (ω) and the sixth harmonic (6ω) by a sum-frequency generation (7ω=ω+6ω). The seventh harmonic, which has been generated in wavelength conversion at the CBO crystal 34, and the fundamental wave (ω), which has passed through the crystal 34 without wavelength conversion, are separated by a dichroic mirror 55. The seventh harmonic (7ω) is reflected by the dichroic mirror 55 and led through another mirror 57, a condenser lens 47 and another dichroic mirror 58 to a fifth wavelength conversion crystal 35. On the other hand, the fundamental wave (ω) passes through the dichroic mirror 55, and its polarization is rotated by 90 degrees at a wave plate 49. Then, it is passed through a condenser lens 46 and combined coaxially with the seventh harmonic by a dichroic mirror 58 and fed into the wavelength conversion crystal 35 of a fifth wavelength-converting section. Incidentally, instead of the CBO crystal, a CLBO crystal or a BBO crystal can be used.

The fifth wavelength-converting section comprises a CLBO crystal as the wavelength conversion crystal 35, which is used under angular phase matching condition to generate the eighth harmonic (8ω, λ=193.4 nm) from the fundamental wave (ω) and the seventh harmonic (7ω) by a sum-frequency generation (8ω=ω+7ω). Incidentally, instead of the CLBO crystal, an LBO crystal may be used.

In this way, the fundamental wave laser light (amplified signal light) Lr having a wavelength λ=1547 nm, which is input from the optical amplifier 20 to the wavelength-converting optical system 30, undergoes sequential wavelength conversions while it is passing through the five wavelength-converting sections, and it is output as an ultraviolet laser light Lv having a wavelength λ=193 nm, which is the eighth harmonic of the fundamental wave. As the wavelength-converting optical system 30 performs wavelength conversions utilizing the property of the signal light input therein, it can output ultraviolet light at a high peak power and a high average power.

Figure 6:
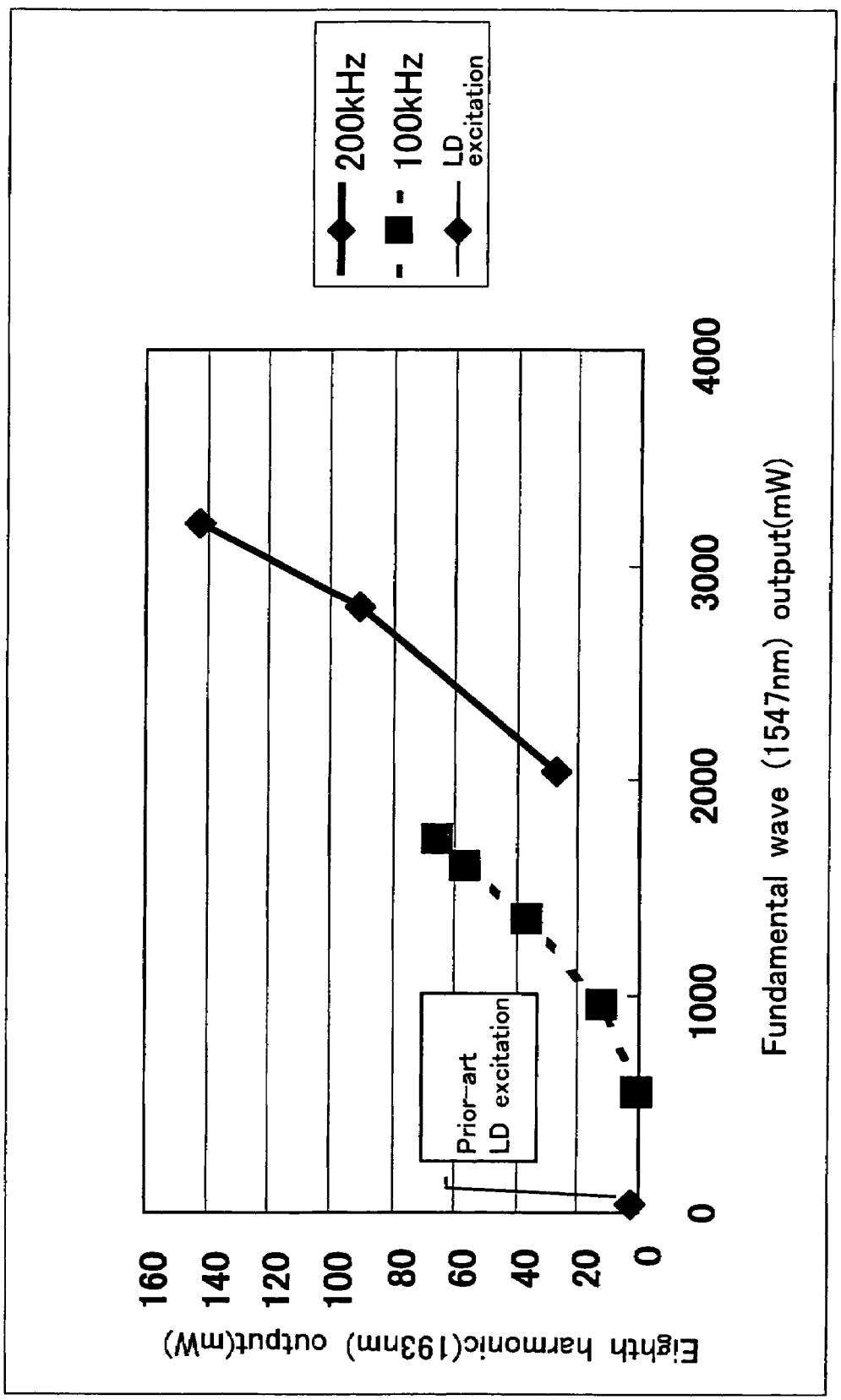
FIG. 6 is a graph describing a relation between the power of a fundamental wave having wavelength 1547 nm and that of the eighth harmonic of the fundamental wave, which has a wavelength of 193 nm.

FIG. 6 is a graph describing a relation between the power of a fundamental wave having a wavelength 1547 nm and that of the eighth harmonic of the fundamental wave, which has a wavelength of 193 nm. The efficiency of the conversion from the fundamental wave having 1547 nm to the eighth harmonic having 193 nm is about 4.5%, which is relatively high, and this indicates that the fundamental wave light has a high quality.

It is clear from the ultraviolet light source 1 described above that the present invention provides an all solid state ultraviolet light source which has a simple and compact construction and therefore does not require complicated maintenance work and which can output ultraviolet light at a high peak power and a high average power.

In the above described embodiment, a DFB semiconductor laser, which operates at an oscillation wavelength of λ=1547 nm in an infrared range, is used as an example of laser light source 10, which generates the signal light. Also, the wavelength-converting optical system 30 is illustrated as an arrangement that comprises five wavelength conversion crystals for converting the fundamental wave into the eighth harmonic having a wavelength λ=193.4 nm, which is equal to that generated by an ArF excimer laser. However, the laser light source 10 may be an Er-YAG laser or a laser for a visible light range, and the wavelength-converting optical system may comprise another well-known crystal arrangement (for example, fundamental waveω→2ω→4ω→8ω) or may take a fiber configuration. Moreover, the wavelength of the ultraviolet light emitted from the ultraviolet light source is not limited to a band at 193 nm. It may be, for example, in a 248 nm band, which is substantially equal to that generated by a KrF excimer laser, or in a 157 nm band, which is substantially equal to that generated by an $F_2$ laser.

Laser Treatment Apparatus

Now, laser treatment apparatus that comprises the ultraviolet light source 1 according to the present invention, which has been described above, is described in reference to FIG. 7 and FIG. 8. The laser treatment apparatus 5 is an apparatus for treating such disorders as myopia and astigmatism by correcting irregularities in the convexity and concavity or curvature of the cornea. In this case, the cornea is irradiated with an ultraviolet laser light for a cornea-ectal ablation in Photorefractive Keratectomy (PRK) or for an inner ablation of the incised cornea in Laser Intrastromal Keratomileusis (LASIK).

Figure 7:
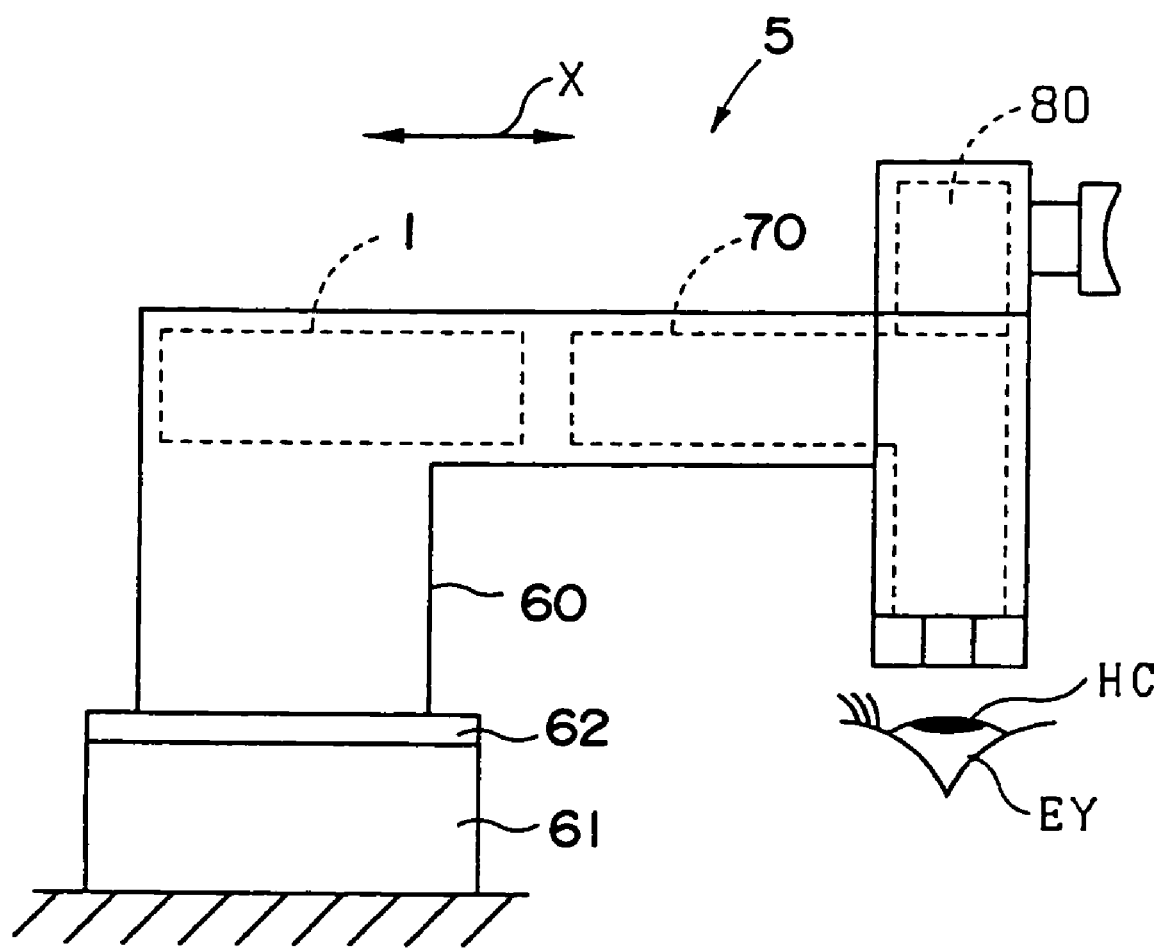
FIG. 7 is a schematic diagram showing laser treatment apparatus according to the present invention.

As shown in the FIG. 7, the laser treatment apparatus 5 basically comprises in an apparatus housing 60 an ultraviolet light source 1, which is described above, an irradiation optical system 70, which leads an ultraviolet laser light Lv output from the ultraviolet light source 1 to the surface (treatment site) of the cornea HC of an eyeball EY for irradiation, and an observation optical system 80, which is used for observation of the treatment site.

The apparatus housing 60 is mounted on an X-Y stage 62 on a base 61, so the apparatus housing 60 as a whole is movable with respect to the eyeball EY in the direction indicated by arrow X, i.e., the right and left direction in FIG. 7 and in the direction perpendicular to the plane of the page carrying the drawing, i.e., the Y direction.

Figure 8:
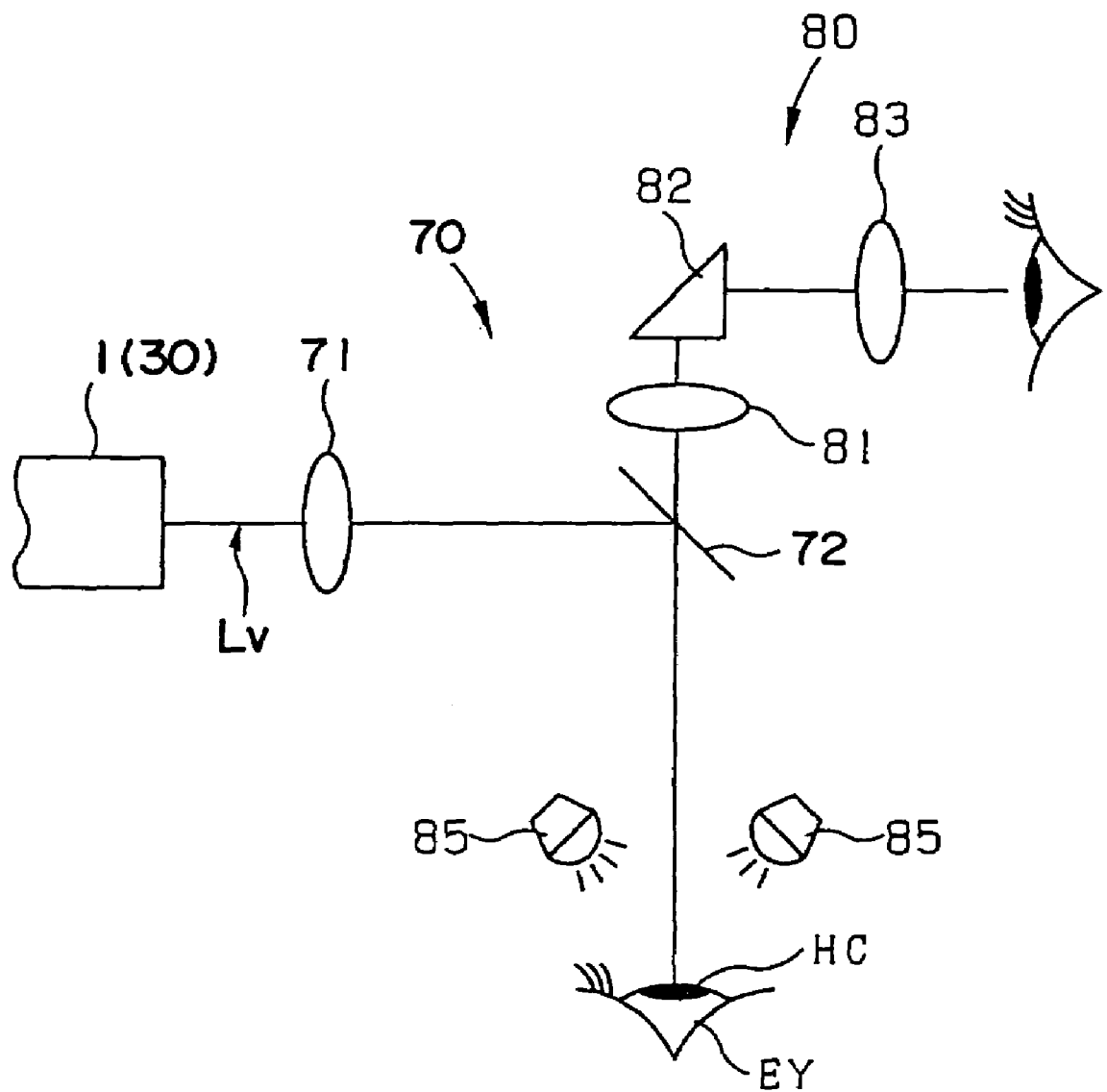
FIG. 8 is a schematic diagram showing an irradiation optical system and an observation optical system of the laser treatment apparatus.

FIG. 8 shows the construction of the irradiation optical system 70 and that of the observation optical system 80. The irradiation optical system 70 comprises a condenser lens 71, which collects the ultraviolet laser light Lv having a wavelength λ=193 nm emitted from the ultraviolet light source 1 to form a spot with a predetermined diameter on the eyeball EY, and a dichroic mirror 72, which reflects the ultraviolet laser light from the condenser lens 71 so as to irradiate the surface of the cornea HC of the eyeball EY as an object to be treated. The dichroic mirror 72 is set to reflect light in the ultraviolet range and to pass light in the visible range through. Therefore, the ultraviolet laser light Lv is reflected and aligned coaxial to the optical axis of the observation optical system 80, which is described below, for the irradiation of the cornea HC surface.

On the other hand, the observation optical system 80 comprises an illumination lamp 85, which illuminates the surface of the cornea HC of the eyeball EY, which is being treated, an objective lens 81, which receives the visible light that has originated from the illumination lamp 85 and has reflected by the cornea HC and then has passed through the dichroic mirror 72, a prism 82, which reflects the light coming from the objective lens 81, and an eyepiece 83, which receives the light reflected by the prism for an image-formation. The operator can see a magnified image of the cornea HC through the eyepiece 83.

With this apparatus, the operator, for example, an ophthalmologist, can perform a laser treatment while he or she is watching through the observation optical system 80. For example, while the operator is observing the eyeball EY, he or she shifts the apparatus housing 60 in the X coordinate and in the Y coordinate and irradiates the surface of the cornea HC, which is an object to be treated, with a spotlighting ultraviolet laser light to cause a ablation in the irradiated area. The movement of the X-Y coordinate table 62 is controlled by an operation controller (not shown) so that the apparatus housing 60 is shifted in the X coordinate and the Y coordinate, moving the spotlight, which is projected on the surface of the cornea HC. Therefore, a corneaectal ablation is performed accurately as a treatment correcting such as myopia or astigmatism or hyperopia.

By the way, the size of the ablation in laser treatment changes greatly in correspondence to the power of the ultraviolet laser light Lv irradiating the cornea HC. For this reason, the power of the ultraviolet laser light source 1 is easily adjustable, for example, by controlling the pulse-frequency of the laser light source 10, or by controlling the power of the excitation light of the optical amplifier 20. Furthermore, the ultraviolet laser light can be turned ON and OFF by controlling the ON-OFF of the DFB semiconductor laser of the laser light source 10. Otherwise, for this purpose, simply, a modulating element, for example, an electro-optic modulating element or an acousto-optic modulating element, or a mechanical shutter is provided for the optical path.

Clearly from the above described laser treatment apparatus, the present invention provides laser treatment apparatus that is advantageous in maintenance and operability besides being compact and light-weight.

Exposure Apparatus

Figure 9:
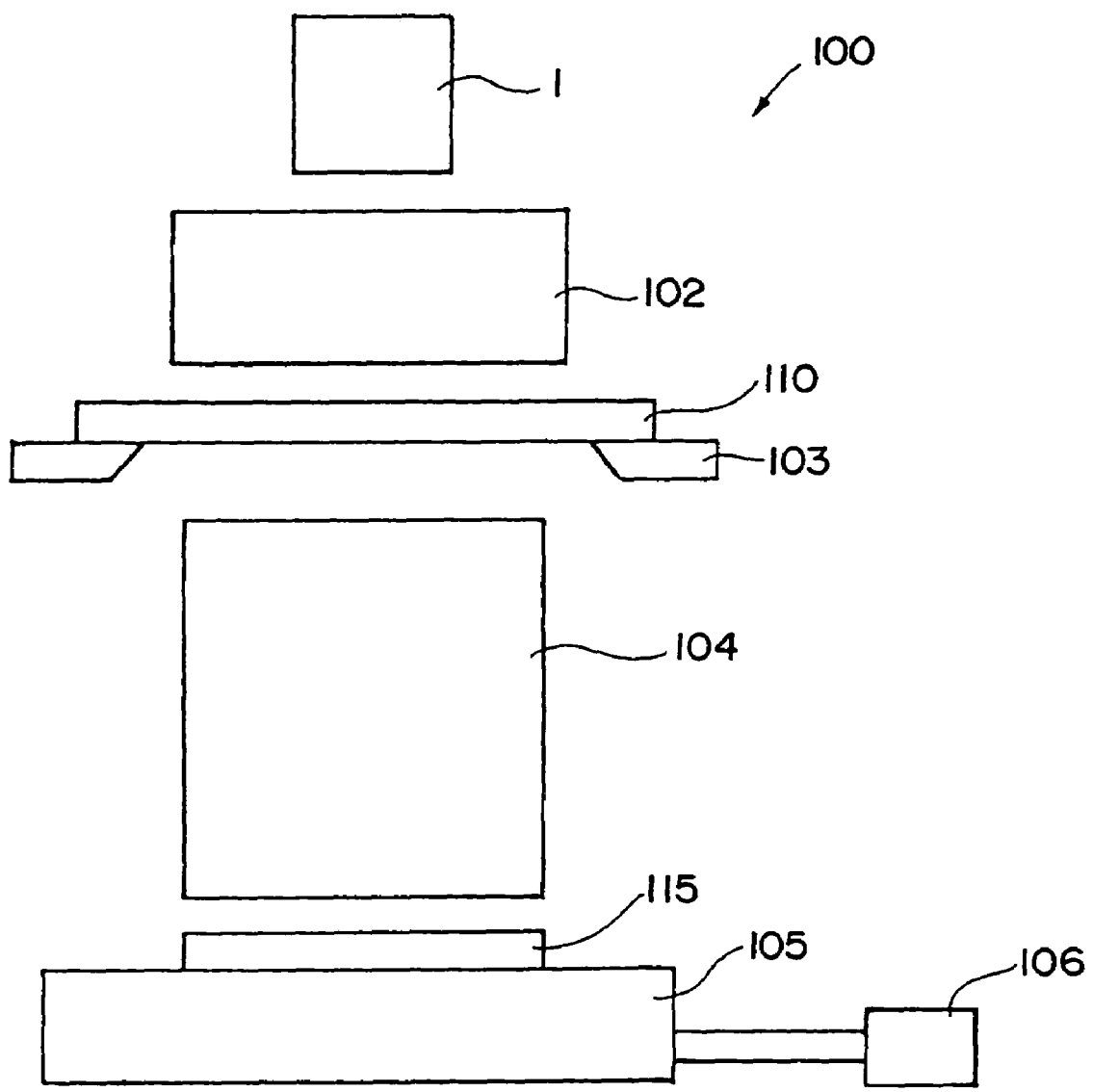
FIG. 9 is a schematic diagram showing an exposure apparatus according to the present invention.

Now, exposure apparatus 100, which comprises the above described ultraviolet light source 1 and is used for a photolithography in semiconductor-device production process, is described in reference to FIG. 9. Exposure apparatus, which is used in photolithographic process, is in principle similar to photoengraving, and it optically transfers a circuit pattern, which is described precisely on a photomask (reticle), onto a semiconductor wafer or a glass substrate, which is coated with a photoresist in a reduction projection manner. The exposure apparatus 100 comprises the above mentioned ultraviolet light source 1, an illumination optical system 102, a mask-supporting table 103 for supporting a photomask (reticle) 110, a projection optical system 104, a wafer-carrying table 105, which supports a semiconductor wafer 115 as an object to be exposed, and a driving device 106, which shifts the wafer-carrying table 105 horizontally.

In the exposure apparatus 100, the ultraviolet laser light Lv output from the above described ultraviolet light source 1 is incident on the illumination optical system 102, which comprises a plurality of lenses. The ultraviolet laser light after passing through the illumination optical system 102 illuminates the whole surface of the photomask 110, which is supported by the mask-supporting table 103. The light passing through the photomask 110 has an image of the circuit pattern, which is described on the photomask 110, and this image is projected through the projection optical system 104 onto a predetermined part of the semiconductor wafer 115, which is placed on the wafer-carrying table 105. In this case, the circuit pattern on the photomask is subjected to reduction and is projected on the semiconductor wafer 115 by the projection optical system 104.

The amount of illumination light of the exposure apparatus is easily adjustable, for example, by controlling the pulse-frequency of the laser light source 10, or by controlling the power of the excitation light of the optical amplifier 20. Furthermore, the ultraviolet laser light can be turned ON and OFF by controlling the ON-OFF of the DFB semiconductor laser of the laser light source 10. Otherwise, for this purpose, simply, a modulating element, for example, an electro-optic modulating element or an acousto-optic modulating element, or a mechanical shutter can be provided to control the optical path.

It is clear from the above described exposure apparatus that the present invention provides exposure apparatus which is advantageous in compactness, maintenance and operability because it utilizes a small and light-weight ultraviolet light source, the apparatus offering a high degree of freedom in the placement of the ultraviolet light source.

As described above, an ultraviolet light source according to the present invention comprises a single mode fiber laser as an excitation light source for a fiber optical amplifier. With this simple construction, the ultraviolet light source achieves both a high peak power and a high average power.

Mask Defect-inspection Apparatus

Figure 10:
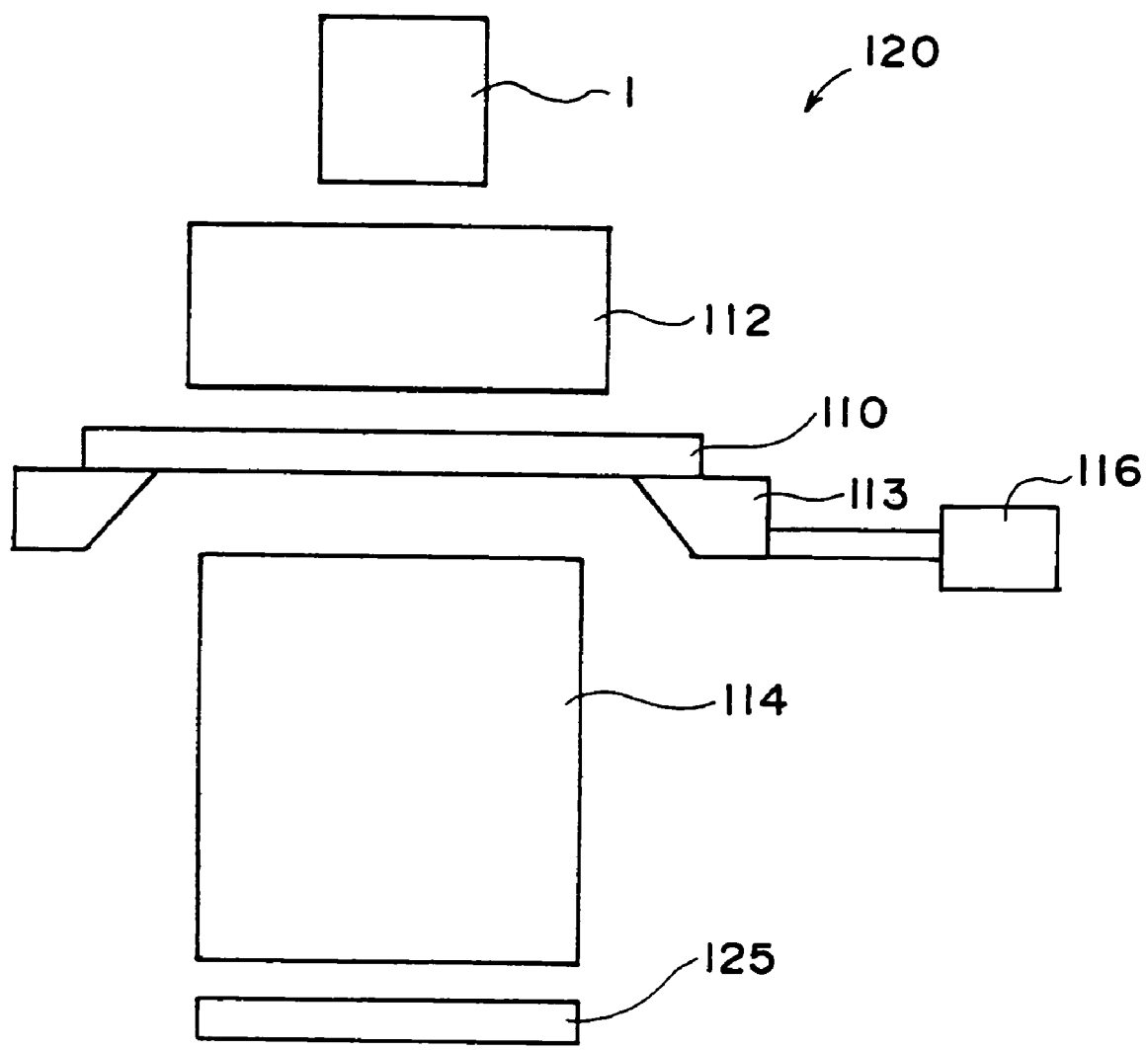
FIG. 10 is a schematic diagram showing a mask-defect inspection apparatus according to the present invention.

Now, mask defect-inspection apparatus comprising the above described ultraviolet light source 1 according to the present invention is described in reference to FIG. 10.

The mask defect-inspection apparatus optically projects a circuit pattern, which is described precisely on a photomask, onto a Time Delay and Integration (TDI) sensor, compares a sensor image with a predetermined reference image, and detects a defect from the difference between these images.

The mask defect-inspection apparatus 120 comprises the above mentioned ultraviolet light source 1, an illumination optical system 112, a mask-supporting table 113 for supporting a photomask 110, a driving device 116, which shifts the mask-supporting table 113 horizontally, a projection optical system 114, and a TDI sensor 125.

In the mask defect-inspection apparatus 120, the ultraviolet laser light Lv output from the above described ultraviolet light source 1 is incident on the illumination optical system 112, which comprises a plurality of lenses. The ultraviolet laser light after passing through the illumination optical system 112 illuminates a predetermined area of the photomask 110, which is supported by the mask-supporting table 113. The light passing through the photomask 110 has an image of the circuit pattern, which is described on the photomask 110, and this image is projected through the projection optical system 114 onto the TDI sensor 125 at a predetermined position thereof. Incidentally, the speed of the horizontal movement of the mask-supporting table 113 is synchronized to the transfer timing of the TDI sensor 125.

What is claimed is:

1. An ultraviolet light source comprising:
   a laser light source, which generates light in an infrared-to-visible range, an optical amplifier, which comprises a plurality of stages of fiber optical amplifiers for amplifying the light generated by the laser light source sequentially; and a wavelength-converting optical system, which comprises at least one wavelength conversion crystal and converts the light amplified by the optical amplifier into ultraviolet light as an output, wherein the plurality of stages of fiber optical amplifiers includes a final stage of fiber optical amplifier having an excitation light source made by a single mode fiber laser, and the light input into the final stage of fiber optical amplifier which is amplified by the upstream stages of said fiber optical amplifier is mixed coaxially with the excitation light from the single mode fiber laser by a Wavelength Division Multiplexer (WDM) provided at an input port of the final stage of fiber optical amplifier.

2. The ultraviolet light source set forth in claim 1, wherein the single mode fiber laser comprises a Raman fiber laser.

3. The ultraviolet light source set forth in claim 1, wherein the single mode fiber laser comprises an ytterbium-doped fiber laser.

4. The ultraviolet light source set forth in claim 1, wherein the wavelength division multiplexer comprises a fiber-fused type wavelength division multiplexer.

5. The ultraviolet light source set forth in claim 1, wherein the final stage fiber optical amplifier comprises a single clad fiber amplifier with high erbium concentration and a large mode radius of about 10 μm or more.

6. The ultraviolet light source set forth in claim 1, wherein the laser light source comprises a Distributed Feedback (DFB) semiconductor laser.

7. The ultraviolet light source set forth in claim 1, wherein the light passing through the WDM has a peak power of about 1 kW or more.

8. A laser treatment apparatus comprising:
an ultraviolet light source set forth in claim 1; and
an irradiation optical system, which leads ultraviolet light emitted from the ultraviolet light source to a treatment site for irradiation.

9. An exposure apparatus comprising:
an ultraviolet light source set forth in claim 1;
a mask-supporting part, which supports a photomask provided with a predetermined exposure pattern;
an object supporting part, which supports an object to be exposed;

an illumination optical system, which leads ultraviolet light emitted from the ultraviolet light source to illuminate the photomask supported by the mask-supporting part; and a projection optical system, which leads the light that has passed through the photomask in the illumination through the illumination optical system, to project the object to be exposed, which is supported by the object supporting part.

10. A mask defect-inspection apparatus comprising: an ultraviolet light source set forth in claim 1;
a mask-supporting part, which supports a photomask provided with a predetermined pattern;
a detector, which detects an image of the predetermined pattern;
an illumination optical system, which leads ultraviolet light emitted from the ultraviolet light source to illuminate the photomask supported by the mask-supporting part; and
a projection optical system, which leads the ultraviolet light that has passed through the photomask in the illumination through the illumination optical system, to project the image onto the detector.

11. An exposure apparatus comprising:
an ultraviolet light source set forth in claim 1;
a mask-supporting part, which supports a photomask provided with a predetermined exposure pattern;
an object supporting part, which supports an object to be exposed;
an illumination optical system, which leads ultraviolet light emitted from the ultraviolet light source to illuminate the photomask; and
a projection optical system, which leads the light from the photomask onto the object to be exposed.

12. An inspection apparatus comprising:
an ultraviolet light source set forth in claim 1;
an object-supporting part for supporting an inspected object;
a detector, which detects an image of the object;
an illumination optical system, which leads ultraviolet light emitted from the ultraviolet light source to illuminate the object; and
a projection optical system, which leads the ultraviolet light from the object onto the detector.

* * * * *